(12) United States Patent
Watson et al.

(10) Patent No.: US 8,660,799 B2
(45) Date of Patent: Feb. 25, 2014

(54) PROCESSING AND DETECTING BASELINE CHANGES IN SIGNALS

(75) Inventors: James Watson, Dunfermline (GB); Paul Stanley Addison, Edinburgh (GB)

(73) Assignee: Nellcor Puritan Bennett Ireland, Galway (IE)

( * ) Notice: Subject to any disclaimer, the term of this patent is extended or adjusted under 35 U.S.C. 154(b) by 1514 days.

(21) Appl. No.: 12/245,400

(22) Filed: Oct. 3, 2008

(65) Prior Publication Data

US 2009/0326353 A1  Dec. 31, 2009

Related U.S. Application Data

(60) Provisional application No. 61/077,036, filed on Jun. 30, 2008, provisional application No. 61/077,130, filed on Jun. 30, 2008.

(51) Int. Cl.
*G01N 33/48* (2006.01)
*G01N 33/50* (2006.01)
*G06F 7/60* (2006.01)
*G06F 17/10* (2006.01)
*G06F 19/00* (2011.01)

(52) U.S. Cl.
CPC ..................................... *G06F 19/34* (2013.01)
USPC .................................. 702/19; 702/20; 703/3

(58) Field of Classification Search
None
See application file for complete search history.

(56) References Cited

U.S. PATENT DOCUMENTS

| | | |
|---|---|---|
| 3,835,840 A | 9/1974 | Mount |
| 4,112,930 A | 9/1978 | Feldman |
| 4,289,141 A | 9/1981 | Cormier |
| 4,561,447 A | 12/1985 | Kawamura et al. |
| 4,676,253 A | 6/1987 | Newman |
| 4,729,382 A | 3/1988 | Schaffer |
| 4,830,017 A | 5/1989 | Perry |
| 4,836,213 A | 6/1989 | Wenzel et al. |
| 4,854,327 A | 8/1989 | Kunig |
| 4,898,176 A | 2/1990 | Petre |
| 4,924,871 A | 5/1990 | Honeyager |
| 4,928,700 A | 5/1990 | Harada |
| 4,951,679 A | 8/1990 | Harada |
| 4,976,268 A | 12/1990 | Kurosawa et al. |
| 4,987,900 A | 1/1991 | Eckerle |
| 5,050,614 A | 9/1991 | Logan |
| 5,065,765 A | 11/1991 | Eckerle |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada |
| 5,163,328 A | 11/1992 | Holland |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,309,917 A | 5/1994 | Wang |
| 5,431,159 A | 7/1995 | Baker |
| 5,439,483 A | 8/1995 | Duong-Van |
| 5,450,852 A | 9/1995 | Archibald et al. |
| 5,467,771 A | 11/1995 | Narimatsu |
| 5,490,506 A | 2/1996 | Takatani |
| 5,494,043 A | 2/1996 | O'Sullivan et al. |
| 5,497,779 A | 3/1996 | Takaya |
| 5,505,209 A | 4/1996 | Reining |
| 5,533,511 A | 7/1996 | Kaspari |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan |
| 5,590,650 A | 1/1997 | Genova |
| 5,617,868 A | 4/1997 | Harada |
| 5,632,272 A | 5/1997 | Diab et al. |
| 5,640,964 A | 6/1997 | Archibald et al. |
| 5,649,542 A | 7/1997 | Archibald et al. |
| 5,649,543 A | 7/1997 | Hosaka et al. |
| 5,676,140 A | 10/1997 | Ukawa |
| 5,682,898 A | 11/1997 | Aung |
| 5,685,316 A | 11/1997 | Schookin et al. |

(Continued)

FOREIGN PATENT DOCUMENTS

| | | |
|---|---|---|
| EP | 0443267 | 8/1991 |
| EP | 0755221 | 1/1997 |

(Continued)

OTHER PUBLICATIONS

International Search Report PCT/IB2009/006134, 6 pages, mailed Jan. 25, 2010.
Leonard P et al: "Standard Pulse Oximeters Can Be Used to Monitor Respiratory Rate" Journal of Accident and Emergency Medicine, BMJ Publishing Group, London, GB, vol. 20, No. 6, Jan. 10, 2003.
Addison P S et al: "Wavelet Transform Reassignment and the Use of Low-Oscillation Complex Wavelets" Mechanical Systems and Signal Processing, London, GB, vol. 20, No. 6, , Aug. 1, 2006.
Addison, Paul S., The Illustrated Wavelet Transform Handbook, Taylor & Francis Group, 2002.
Addison, Paul, "The Little Wave with the Big Future," Physics World, Mar. 2004, pp. 35-39.

(Continued)

*Primary Examiner* — Russell S Negin
(74) *Attorney, Agent, or Firm* — Shvarts & Leiz LLP

(57) ABSTRACT

According to embodiments, systems and methods for detecting the occurrence of events from a signal are provided. A signal processing system may analyze baseline changes and changes in signal characteristics to detect events from a signal. The system may also detect events by analyzing energy parameters and artifacts in a scalogram of the signal. Further, the system may detect events by analyzing both the signal and its corresponding scalogram.

22 Claims, 14 Drawing Sheets
(2 of 14 Drawing Sheet(s) Filed in Color)

(56) References Cited

U.S. PATENT DOCUMENTS

| | | |
|---|---|---|
| 5,704,362 A | 1/1998 | Hersh et al. |
| 5,709,212 A | 1/1998 | Sugo |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,762,610 A | 6/1998 | Narimatsu |
| 5,772,601 A | 6/1998 | Oka |
| 5,772,602 A | 6/1998 | Sakai |
| 5,776,071 A | 7/1998 | Inukai |
| 5,778,881 A | 7/1998 | Sun et al. |
| 5,785,659 A | 7/1998 | Caro et al. |
| 5,791,347 A | 8/1998 | Flaherty et al. |
| 5,795,304 A | 8/1998 | Sun et al. |
| 5,797,395 A | 8/1998 | Martin |
| 5,797,840 A | 8/1998 | Akselrod |
| 5,797,850 A | 8/1998 | Archibald et al. |
| 5,810,736 A | 9/1998 | Pail |
| 5,827,181 A | 10/1998 | Dias |
| 5,827,195 A | 10/1998 | Lander |
| 5,830,131 A | 11/1998 | Caro et al. |
| 5,832,924 A | 11/1998 | Archibald et al. |
| 5,833,618 A | 11/1998 | Caro |
| 5,848,970 A | 12/1998 | Voss |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss |
| 5,967,995 A | 10/1999 | Shusterman et al. |
| 6,002,952 A | 12/1999 | Diab |
| 6,004,274 A | 12/1999 | Nolan |
| 6,007,492 A | 12/1999 | Goto et al. |
| 6,011,986 A | 1/2000 | Diab et al. |
| 6,022,320 A | 2/2000 | Ogura |
| 6,027,452 A | 2/2000 | Flaherty et al. |
| 6,027,453 A | 2/2000 | Miwa |
| 6,027,455 A | 2/2000 | Inukai et al. |
| 6,036,653 A | 3/2000 | Baba et al. |
| 6,045,509 A | 4/2000 | Caro et al. |
| 6,067,462 A | 5/2000 | Diab |
| 6,083,171 A | 7/2000 | Ono et al. |
| 6,094,592 A | 7/2000 | Yorkey |
| 6,095,984 A | 8/2000 | Amano et al. |
| 6,095,987 A | 8/2000 | Shmulewitz |
| 6,117,075 A | 9/2000 | Barnea |
| 6,129,675 A | 10/2000 | Jay |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,171,257 B1 | 1/2001 | Weil et al. |
| 6,171,258 B1 | 1/2001 | Karakasoglu et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,208,951 B1 | 3/2001 | Kumar et al. |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace |
| 6,293,915 B1 | 9/2001 | Amano et al. |
| 6,299,582 B1 | 10/2001 | Brockway et al. |
| 6,325,761 B1 | 12/2001 | Jay |
| 6,332,867 B1 | 12/2001 | Chen et al. |
| 6,350,242 B1 | 2/2002 | Doten et al. |
| 6,361,501 B1 | 3/2002 | Amano et al. |
| 6,371,921 B1 | 4/2002 | Caro |
| 6,393,311 B1 | 5/2002 | Edgar, Jr. et al. |
| 6,443,905 B1 | 9/2002 | Nissila et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,524,240 B1 | 2/2003 | Thede |
| 6,561,986 B2 | 5/2003 | Baura |
| 6,589,185 B1 | 7/2003 | Archibald et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,608,934 B2 | 8/2003 | Scheirer |
| 6,626,839 B2 | 9/2003 | Doten et al. |
| 6,631,281 B1 | 10/2003 | Kastle |
| 6,645,156 B2 | 11/2003 | Oka |
| 6,654,623 B1 | 11/2003 | Kastle |
| 6,658,277 B2 | 12/2003 | Wasserman |
| 6,684,090 B2 | 1/2004 | Ali et al. |
| RE38,476 E | 3/2004 | Diab et al. |
| 6,699,194 B1 | 3/2004 | Diab |
| 6,767,328 B2 | 7/2004 | Kulik |
| 6,773,397 B2 | 8/2004 | Kelly |
| 6,783,498 B2 | 8/2004 | Sackner |
| 6,810,277 B2 | 10/2004 | Edgar, Jr. et al. |
| 6,816,741 B2 | 11/2004 | Diab |
| 6,822,564 B2 | 11/2004 | Al-Ali |
| 6,826,419 B2 | 11/2004 | Diab |
| 6,827,688 B2 | 12/2004 | Goto et al. |
| 6,852,083 B2 | 2/2005 | Caro |
| 6,855,112 B2 | 2/2005 | Kao |
| 6,863,652 B2 | 3/2005 | Huang et al. |
| 6,869,403 B2 | 3/2005 | Narimatsu et al. |
| 6,929,610 B2 | 8/2005 | Forstner |
| 6,931,269 B2 | 8/2005 | Terry |
| 6,996,427 B2 | 2/2006 | Ali et al. |
| 7,001,337 B2 | 2/2006 | Dekker |
| 7,004,907 B2 | 2/2006 | Banet |
| 7,020,507 B2 | 3/2006 | Scharf |
| 7,035,679 B2 | 4/2006 | Addison |
| 7,043,293 B1 | 5/2006 | Baura |
| 7,044,918 B2 | 5/2006 | Diab |
| 7,054,453 B2 | 5/2006 | Causevic |
| 7,054,454 B2 | 5/2006 | Causevic |
| 7,070,566 B2 | 7/2006 | Medero et al. |
| 7,074,192 B2 | 7/2006 | Friedman et al. |
| 7,079,035 B2 | 7/2006 | Bock et al. |
| 7,079,888 B2 | 7/2006 | Oung |
| 7,087,025 B2 | 8/2006 | Baruch |
| 7,171,269 B1 | 1/2007 | Addison |
| 7,173,525 B2 | 2/2007 | Albert |
| 7,184,809 B1 | 2/2007 | Sterling |
| 7,203,267 B2 | 4/2007 | De Man et al. |
| 7,215,984 B2 | 5/2007 | Diab et al. |
| 7,215,986 B2 | 5/2007 | Diab et al. |
| 7,225,013 B2 | 5/2007 | Geva et al. |
| 7,252,636 B2 | 8/2007 | Brown |
| 7,254,500 B2 | 8/2007 | Makeig |
| 7,289,835 B2 | 10/2007 | Mansfield |
| 7,320,030 B2 | 1/2008 | Brown |
| 7,335,162 B2 | 2/2008 | Eide |
| 7,376,238 B1 | 5/2008 | Rivas et al. |
| 7,390,300 B2 | 6/2008 | Inukai |
| 7,390,301 B2 | 6/2008 | Skrabal |
| 7,393,327 B2 | 7/2008 | Inukai |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 7,515,949 B2 | 4/2009 | Norris |
| 7,519,488 B2 | 4/2009 | Fu |
| 7,523,011 B2 | 4/2009 | Akiyama et al. |
| 2003/0163057 A1 | 8/2003 | Flick et al. |
| 2003/0167012 A1* | 9/2003 | Friedman et al. ............ 600/506 |
| 2005/0043616 A1 | 2/2005 | Chinchoy |
| 2005/0070774 A1 | 3/2005 | Addison |
| 2005/0148885 A1 | 7/2005 | Tweed et al. |
| 2005/0251344 A1 | 11/2005 | Appel et al. |

(56) References Cited

U.S. PATENT DOCUMENTS

| | | |
|---|---|---|
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0206021 A1 | 9/2006 | Diab |
| 2006/0209631 A1 | 9/2006 | Melese et al. |
| 2006/0211930 A1 | 9/2006 | Scharf et al. |
| 2006/0217614 A1 | 9/2006 | Takala et al. |
| 2006/0217628 A1 | 9/2006 | Huiku |
| 2006/0229519 A1 | 10/2006 | Fujiwara et al. |
| 2006/0241975 A1 | 10/2006 | Brown |
| 2006/0258921 A1 | 11/2006 | Addison et al. |
| 2006/0265022 A1 | 11/2006 | John et al. |
| 2006/0282000 A1 | 12/2006 | Zhang |
| 2006/0285736 A1 | 12/2006 | Brown |
| 2006/0287603 A1 | 12/2006 | Bartnik et al. |
| 2007/0021673 A1 | 1/2007 | Arbel et al. |
| 2007/0066910 A1 | 3/2007 | Inukai et al. |
| 2007/0073120 A1 | 3/2007 | Li et al. |
| 2007/0073124 A1 | 3/2007 | Li et al. |
| 2007/0083093 A1 | 4/2007 | Diab |
| 2007/0118045 A1 | 5/2007 | Naghavi et al. |
| 2007/0167694 A1 | 7/2007 | Causevic et al. |
| 2007/0167851 A1 | 7/2007 | Vitali et al. |
| 2007/0225582 A1 | 9/2007 | Diab et al. |
| 2007/0249467 A1 | 10/2007 | Hong et al. |
| 2007/0282212 A1 | 12/2007 | Sierra et al. |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0045832 A1 | 2/2008 | McGrath |
| 2008/0082018 A1 | 4/2008 | Sackner et al. |
| 2008/0132798 A1 | 6/2008 | Hong et al. |
| 2008/0214903 A1 | 9/2008 | Orbach |
| 2008/0214942 A1 | 9/2008 | Oh et al. |
| 2008/0242955 A1 | 10/2008 | Uutela et al. |
| 2008/0243021 A1 | 10/2008 | Causevic et al. |
| 2009/0048497 A1 | 2/2009 | Keren |

FOREIGN PATENT DOCUMENTS

| | | |
|---|---|---|
| GB | 2 356 250 | 5/2001 |
| GB | 2 356 251 | 5/2001 |
| GB | 2 356 252 | 5/2001 |
| JP | 03-231630 | 10/1991 |
| JP | 06-142082 | 5/1994 |
| JP | 07-136136 | 5/1995 |
| JP | 09-084776 | 3/1997 |
| JP | 03-225268 | 12/2003 |
| WO | WO 01/25802 | 4/2001 |
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Berne, Robert M., Levy, Matthew N., eds., Physiology, 2nd edition, St. Louis, Mosby, 1988, pp. 357-681.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Yamada, Michio, "Wavelet Analysis and Its Application," Journal of the Institute of Electronics, Information and Communication Engineers, vol. 76, No. 5, May 1993, pp. 518-528.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

\* cited by examiner

PROCESSING AND DETECTING BASELINE CHANGES IN SIGNALS

CROSS-REFERENCE TO RELATED APPLICATIONS

This application claims the benefit of U.S. Provisional Application No. 61/077,036 entitled "PROCESSING AND DETECTING BASELINE CHANGES IN SIGNALS" and 61/077130 entitled "SYSTEMS AND METHODS OF SIGNAL PROCESSING," both filed Jun. 30, 2008, which are hereby incorporated by reference herein in their entireties.

SUMMARY

The present disclosure is generally directed to detecting baseline changes in signals and, in an embodiment, detecting events that cause baseline changes in a photoplethysmogram signal (PPG signal) and corresponding changes in wavelet transforms of the PPG signal.

In accordance with the disclosure, methods and systems are provided for detecting baseline changes in signals. In an embodiment, methods and systems are provided for detecting events that cause baseline changes in a PPG signal and corresponding changes in wavelet transforms of the PPG signal.

In an embodiment, a signal processing system may analyze a signal captured from a user. The signal processing system may calculate at least one signal characteristic of the signal. For example, the signal processing system may calculate an average or median value of an AC component of the signal over a selected amount of time or over a selected number of cardiac events (e.g., cardiac cycles).

In addition to calculating the signal characteristics of the signal, the signal processing system may also detect a baseline change in the signal. For example, the signal processing system may calculate short term and/or long term changes in the baseline over time. The signal processing system may detect the rate of change in the baseline when it is changing and/or the percentage change and/or magnitude of change in the baseline between two periods where the baseline is generally constant or is changing below a threshold. In an embodiment, the signal processing system may characterize the shape of the baseline change using a linear (e.g. best-fit line, threshold-crossing) or nonlinear characterization technique (e.g. curve fitting, template matching, adaptive methods etc.).

After calculating the signal characteristics and detecting the baseline change, the signal processing system may calculate at least one signal characteristic subsequent to the baseline change. For example, the signal processing system may analyze the same signal characteristic that was calculated before the baseline change.

After calculating the signal characteristic subsequent to the baseline change, the signal processing system may analyze the baseline change and the signal characteristic to detect an occurrence of an event. For example, the system may determine that the AC component of the signal increased before and after the baseline change. In response to determining the change in the signal characteristic, the signal processing system may determine that an event occurred causing the baseline change (e.g., the user raised his arm).

In an embodiment, the signal processing system may transform the signal captured from a user to generate a transformed signal. For example, the signal processing system may perform a wavelet transform of the signal. After generating the transformed signal, the signal processing system may generate a scalogram based on the transformed signal. The scalogram may include a pulse band, which is a series of dominant coalescing features across the scalogram.

The signal processing system may calculate characteristics of the scalogram. The characteristics may be an energy parameter such as, for example, the average or median energy within the region. The size and shape of the region may be selected in any suitable way. For example, the height and location of the first region may be selected to cover the pulse band (e.g., centered over the ridge of the pulse band). As another example, the height and location of the first region may be fixed to cover the range of scales where the pulse band is expected to be located.

In addition to calculating the characteristics within a region of the scalogram, the signal processing system may detect an artifact within the scalogram. In an embodiment, the artifact may appear as a high energy broad-scale cone. The system may detect the artifact using any suitable techniques, such as, for example, image processing techniques. In addition, the artifact may be detected in response to detecting a large change in the average energy or detecting peak values in the pulse band that are inconsistent with previous peak values.

In response to calculating the characteristics of the scalogram and detecting the artifact within the scalogram, the signal processing system may analyze the calculated characteristics and detected artifact to detect an event. In an embodiment, the signal processing system may monitor the energy parameter within a region of the scalogram over time and the occurrence of artifacts within the scalogram.

In an embodiment, the signal processing system may detect the occurrence of an event using either the calculated characteristics (e.g., energy parameters) or the detected artifact. For example, based at least in part on a portion of the wavelet transform, the signal processing system may calculate or use one or more predetermined thresholds. If the calculated characteristic or detected artifact exceeds a threshold, the signal processing system may determine that an event has occurred.

After detecting an event, the signal processing system may perform an action based on the detected event. For example, the signal processing system may recalibrate a device based on the detected event. As another example, the signal processing system may set a flag of the detected event.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Features of the disclosure, its nature and various advantages, will be apparent upon consideration of the following detailed description, taken in conjunction with the accompanying drawings, in which like reference characters refer to like parts throughout, and in which.

DETAILED DESCRIPTION

Figure 1:
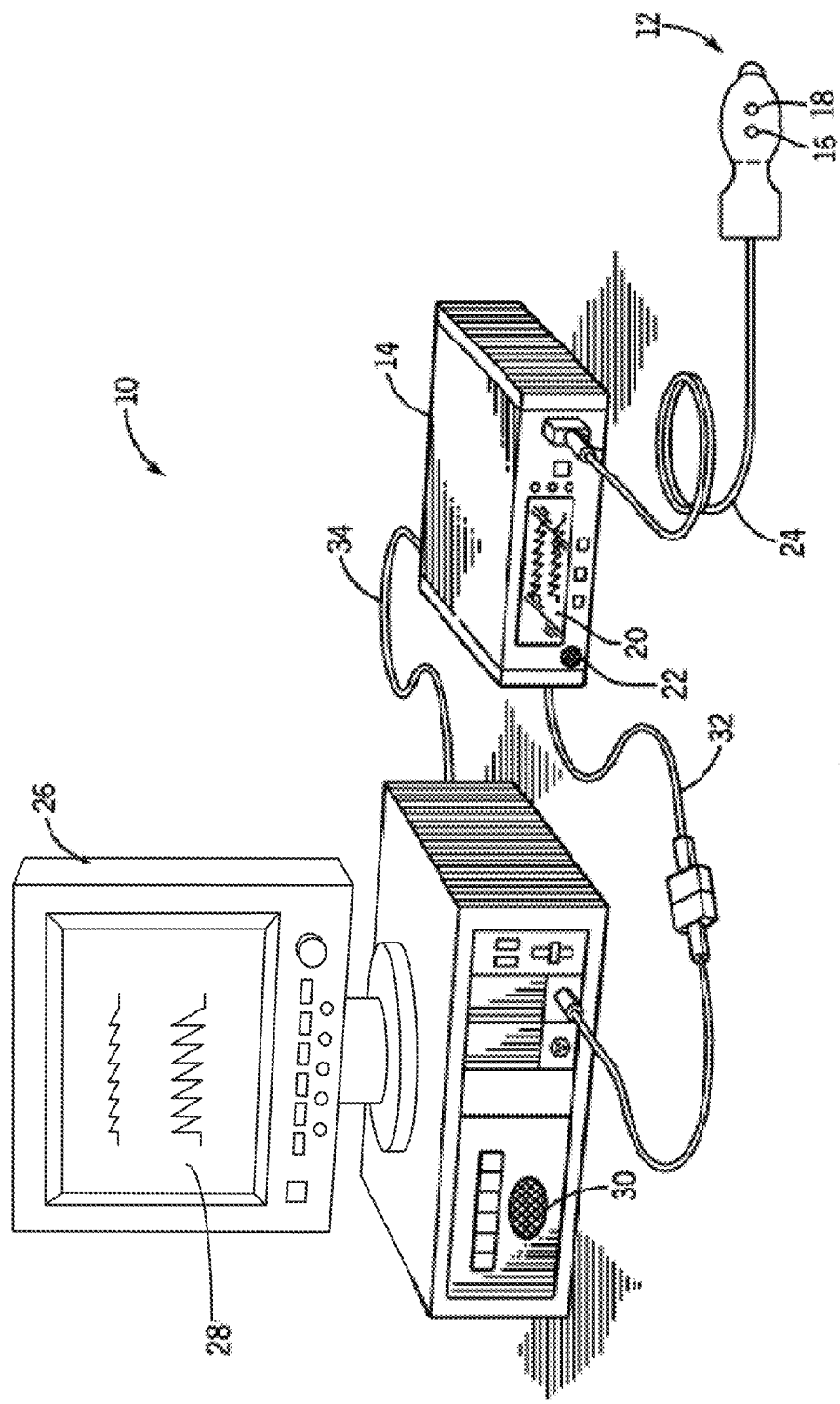
FIG. 1 shows an illustrative pulse oximetry system in accordance with an embodiment.

In medicine, a plethysmograph is an instrument that measures physiological parameters, such as variations in the size of an organ or body part, through an analysis of the blood passing through or present in the targeted body part, or a depiction of these variations. An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patients blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:

$\lambda$=wavelength;

t=time;

I=intensity of light detected;

$I_o$=intensity of light transmitted;

s=oxygen saturation;

$\beta_o$, $\beta_r$=empirically derived absorption coefficients; and l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R) \quad (8)$$

$$y(t) = [I(t_2, \lambda_R) - I(t_1, \lambda_R)]I(t_1, \lambda_{IR})$$

$$y(t) = Rx(t).$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patients tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patients blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
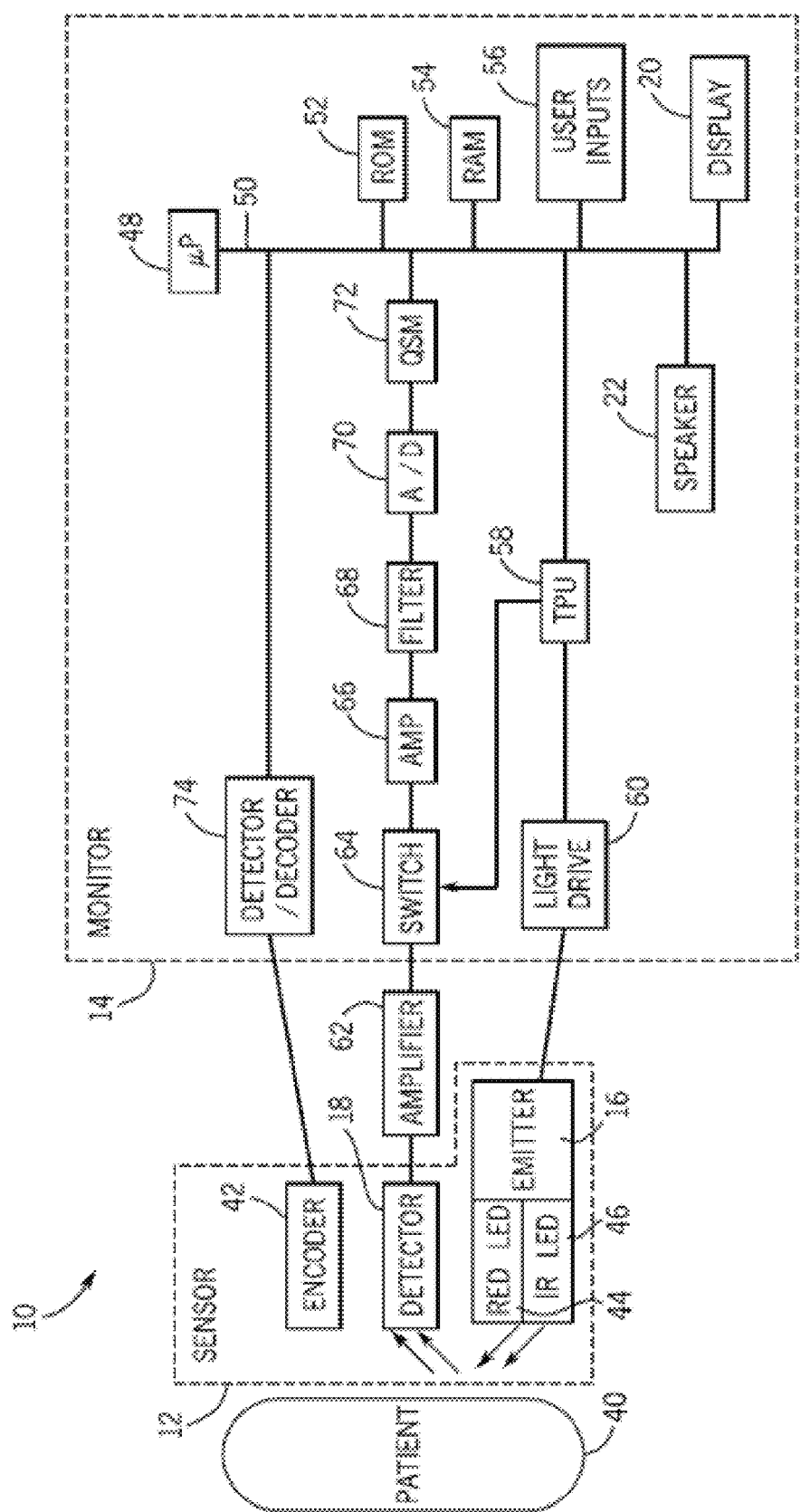
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patients tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patients tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt. \quad (9)$$

where ψ*(t) is the complex conjugate of the wavelet function ψ(t), a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain. As a further example, to reconstruct a temporal signal requires integrating twice, across time and scale, in the wavelet domain while, conversely, one integration across frequency is required to derive a temporal signal from a spectral domain). It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \quad (10)$$

where '∥' is the modulus operator. The scalogram may be rescaled for useful purposes. One common rescaling is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
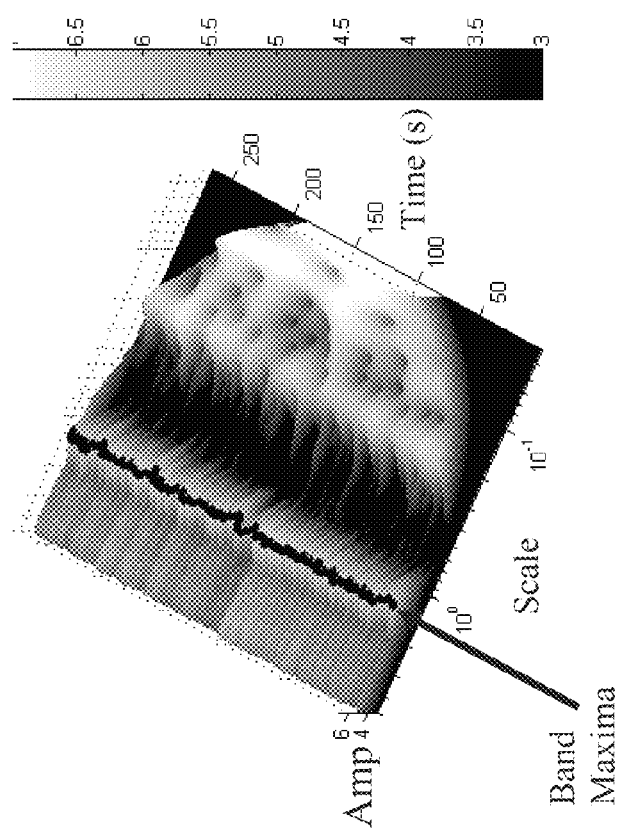
FIGS. 3(a) and 3(b) show illustrative views of a scalogram derived from a PPG signal in accordance with an embodiment.
Figure 3A:
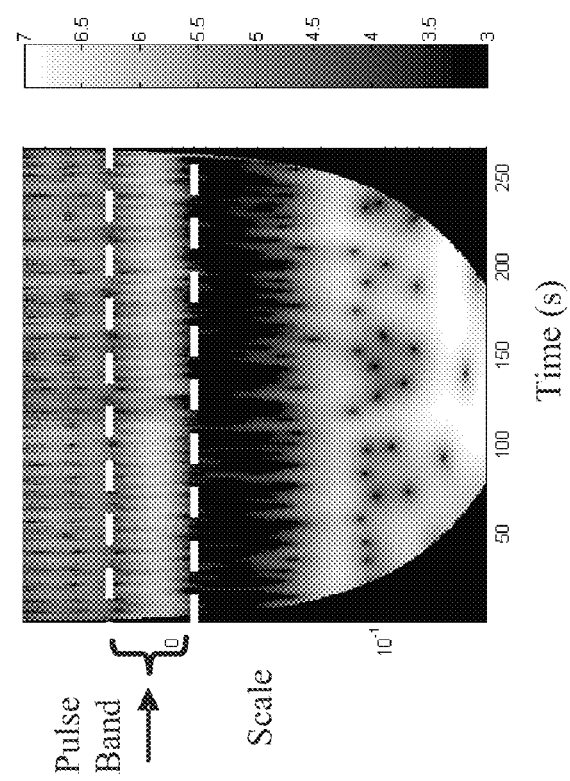

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
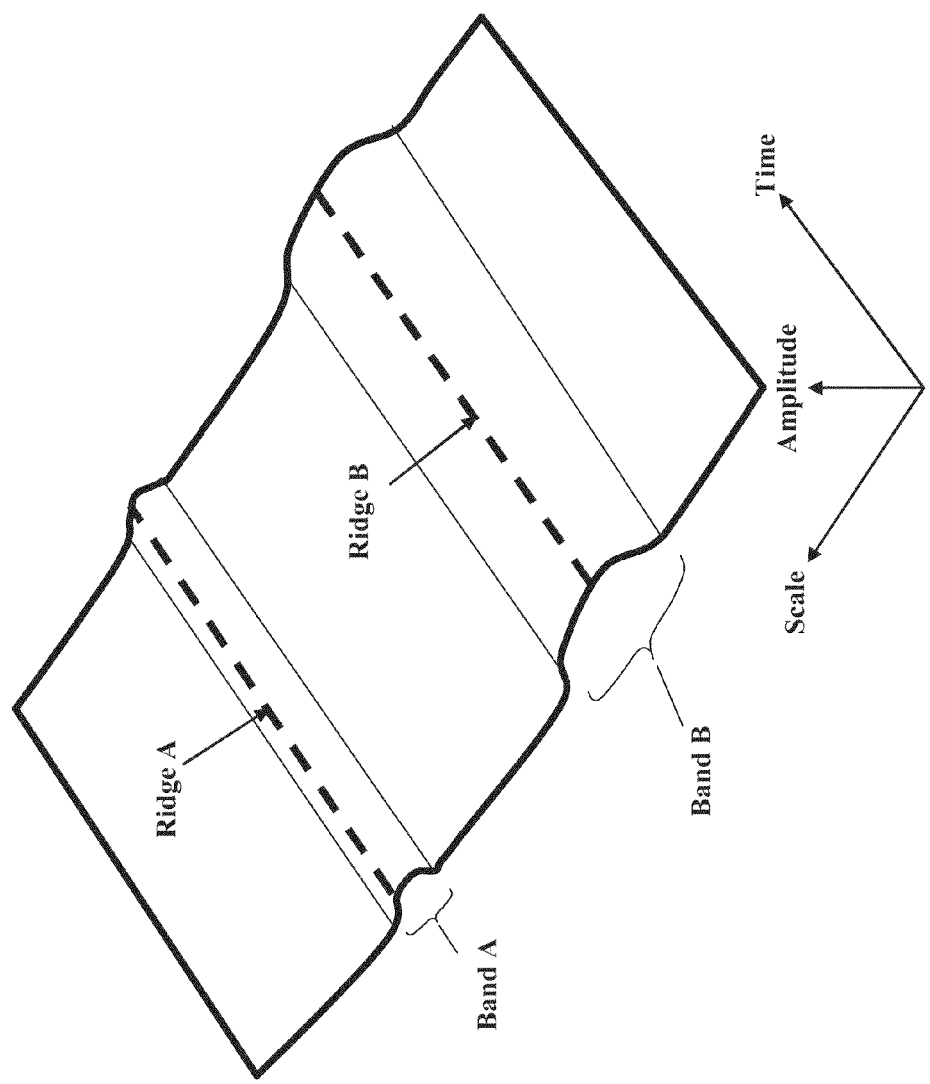
FIG. 3(c) shows an illustrative scalogram derived from a signal containing two pertinent components in accordance with an embodiment.
Figure 3D:
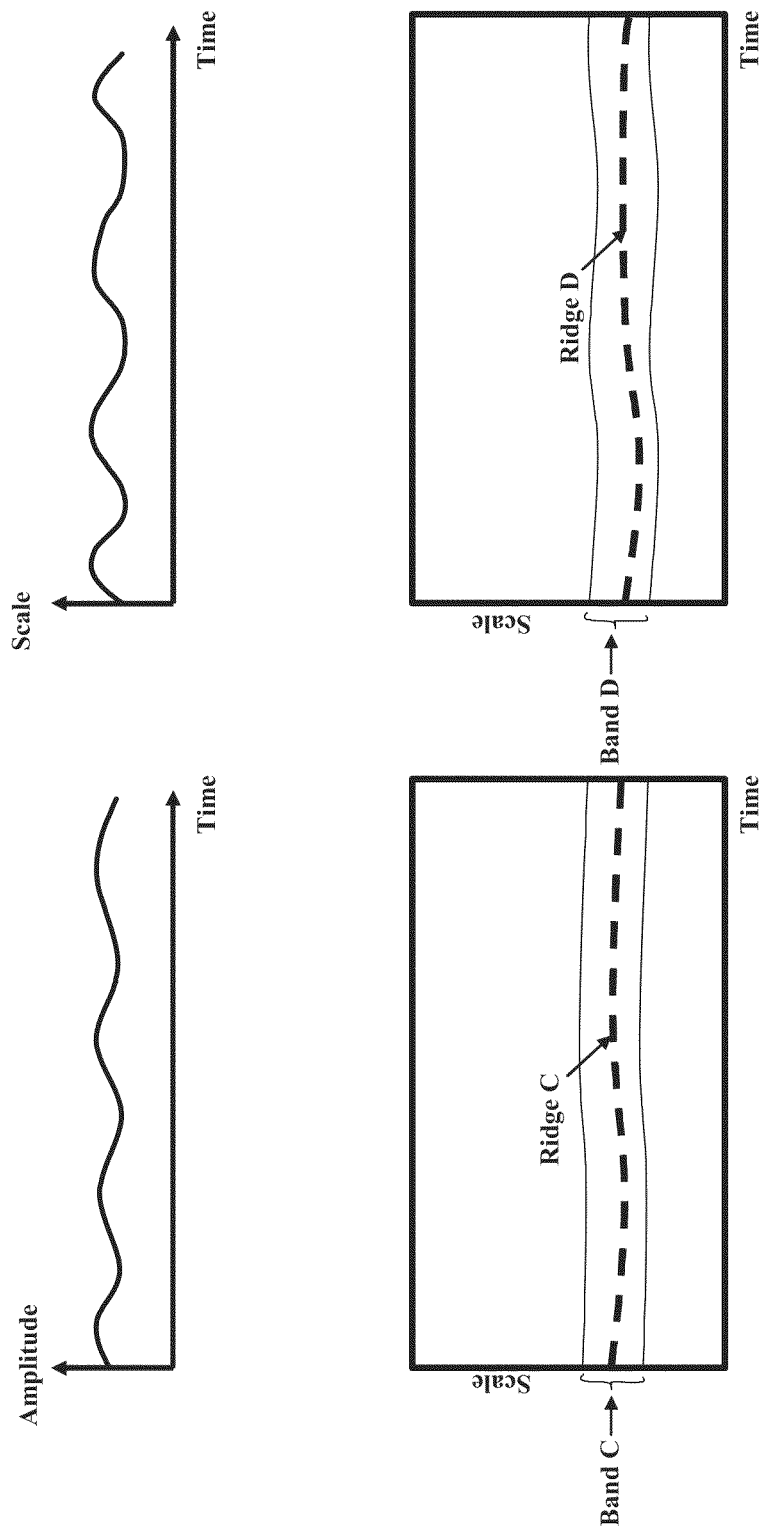
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In an embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\, db}{a^2} \quad (15)$$

which may also be written as:

$$x(t) = \frac{1}{C_g} \int_{-\infty}^{\infty} \int_{0}^{\infty} T(a,b) \psi_{a,b}(t) \frac{da\, db}{a^2} \quad (16)$$

where $C_g$ is a scalar value known as the admissibility constant. It is wavelet type dependent and may be calculated from:

$$C_g = \int_{0}^{\infty} \frac{|\hat{\psi}(f)|^2}{f} df. \quad (17)$$

Figure 3E:
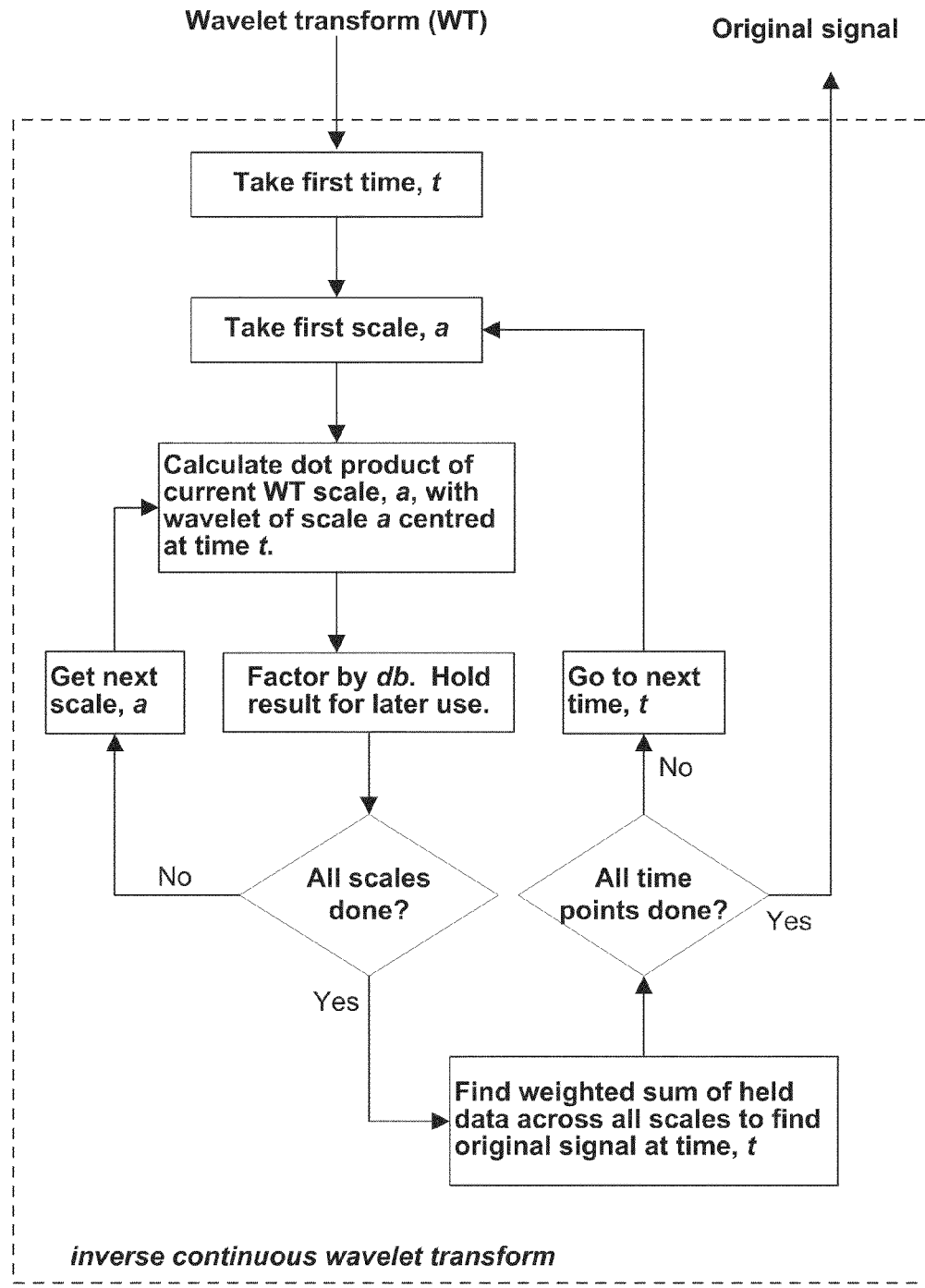
FIGS. 3(e) and 3(f) are flow charts of illustrative steps involved in performing an inverse continuous wavelet transform in accordance with embodiments.
Figure 3F:
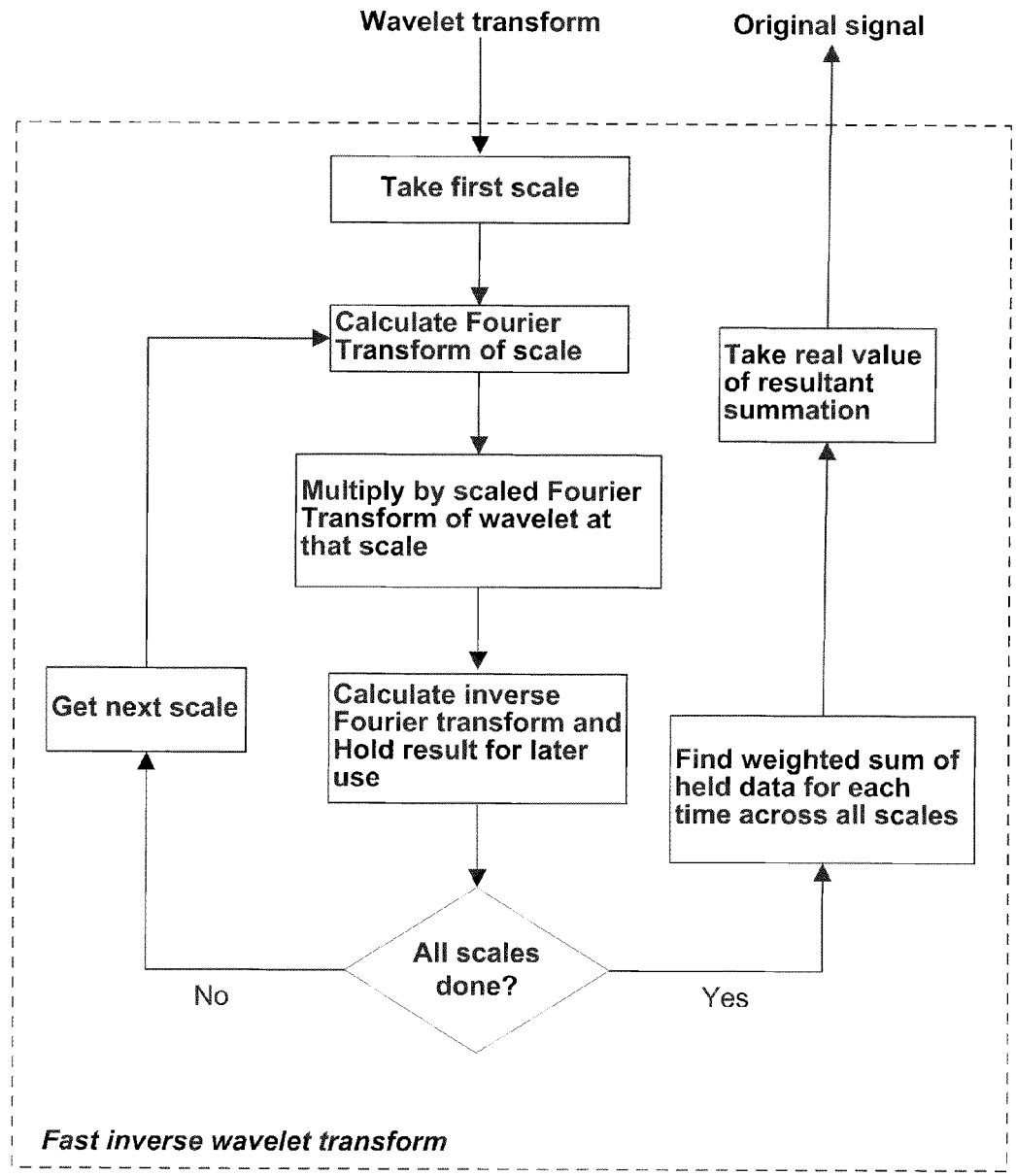

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
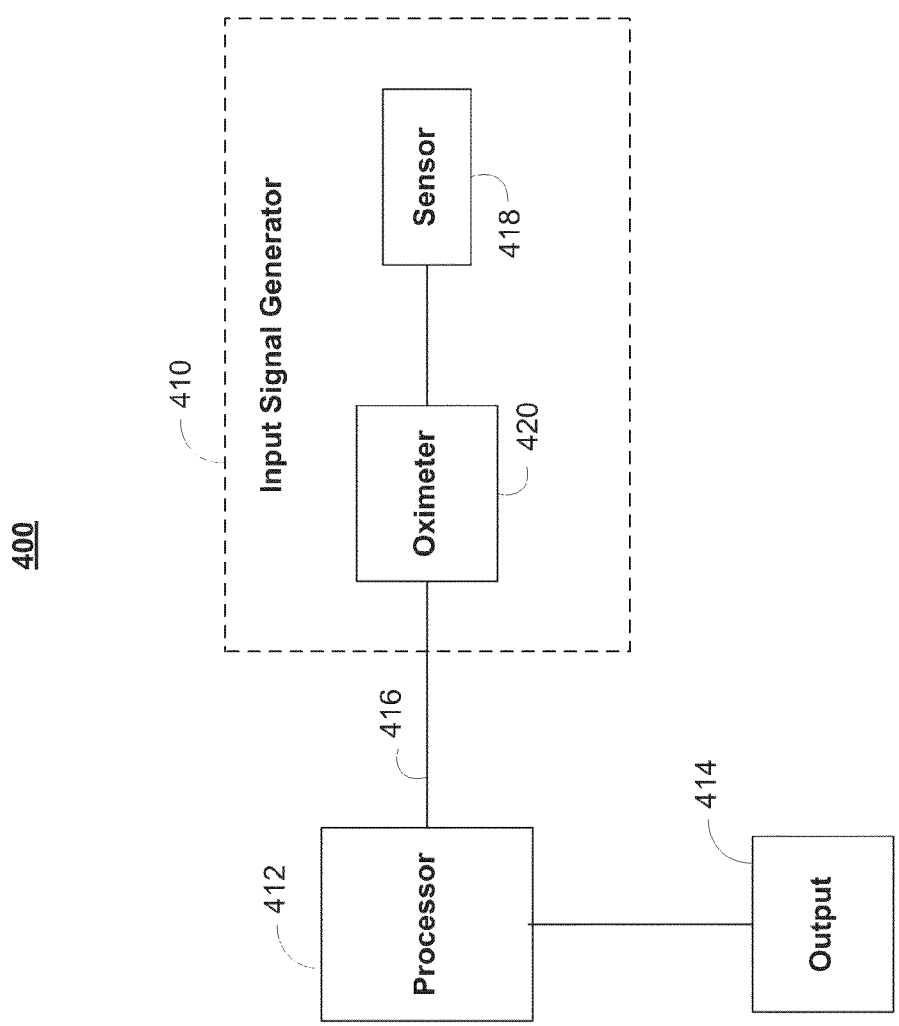
FIG. 4 is a block diagram of an illustrative continuous wavelet processing system in accordance with some embodiments.

FIG. 4 is an illustrative continuous wavelet processing system in accordance with an embodiment. In an embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In an embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5:
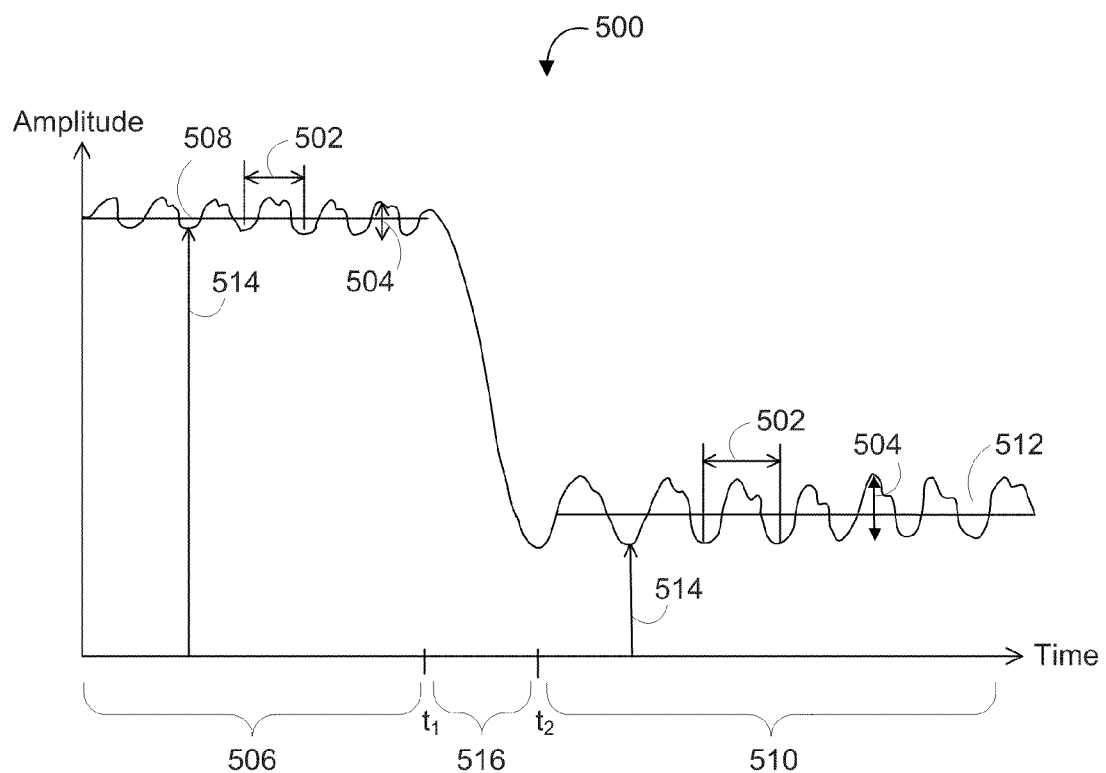
FIG. 5 shows signal characteristics of a PPG signal in accordance with an embodiment.

In accordance with an embodiment, baseline changes and corresponding events may be detected in signals such as PPG signals. FIG. 5 shows an exemplary PPG signal 500 that may be analyzed in accordance with the present disclosure. PPG signal 500 is an oscillating signal having pulses such as pulses 502. Each pulse of PPG signal 500 may correspond to a cardiac cycle. PPG signal 500 has AC component 504, which oscillates around a baseline. For example, as shown in FIG. 5, during time period 506, PPG signal 500 is oscillating around baseline 508. As another example, during time period 510, PPG signal 500 is oscillating around a different baseline 512. The baseline of a signal may be calculated using any suitable technique. For example, the baseline may be calculated as an average of the signal over a selected amount of time or over a selected number of cardiac cycles.

AC component 504 may be caused in part by a change in blood volume at a sensor location. The change in blood volume may be caused by the pressure wave generated by each heart beat. The size of AC component 504 may correspond to the change in blood pressure at the sensor location (e.g., the difference between systolic and diastolic pressure in the arteries). As shown in FIG. 5, the amplitude of AC component 504 is higher during time period 510 than during time period 506. In one example, PPG signal 500 may have been generated using a sensor on a user's finger. During time period 506, the user may have his arm at his side which may cause the arteries to swell due to gravity causing blood to pool in the user's arm. As a result, AC component 504 caused by each heart beat may be small because the expansion in the swollen arteries may be limited. When the user raises his arm above his head during time period 516, gravity caused blood and other body fluids to drain from the arm. As a result, AC component 504 during time period 510 may be greater because the arteries may be able to expand more easily.

In addition to the AC component, PPG signal 500 also has amplitude component 514, which may be attributed to the total amount of absorption and/or transmission between the sensor emitter and detector. FIG. 5 represents an increase in light received at the sensor detector as a decrease in amplitude. As shown in FIG. 5, amplitude component 514 also changes between time period 506 and time period 510. For example, during time period 506, amplitude component 514 oscillates about baseline 508. When the user changes his arm position (e.g., raises his arm) during time period 516, amplitude component 514 may significantly decrease. The decrease may be attributed to a decrease in fluids such as blood within the user's arm as a result of gravity causing fluids to flow out of the arm, thus allowing more light to be received at the sensor detector. Finally, at the beginning of time period 510, amplitude component 514 begins to settle into a new steady state oscillation about baseline 512.

In accordance with an embodiment, by calculating signal characteristics of PPG signal 500 and detecting changes in the baseline and the signal characteristics, an event can be detected by a signal processing system, such as signal processing system 400 of FIG. 4. The signal processing system may calculate a signal characteristic by calculating, for example, a signal characteristic of the AC component of PPG signal 500. The calculated signal characteristic may be any suitable characteristic such as an average or median amplitude of the AC component over a selected amount of time or over a selected number of cardiac events. It will be understood that the signal processing system may use any other suitable algorithm to calculate the desired signal characteristic.

The signal processing system may also calculate the baseline and the baseline changes in PPG signal 500. For example, the signal processing system may continuously or periodically calculate the baseline of PPG signal 500. The signal processing system may also calculate short term and/or long term changes in the baseline over time. For example, in FIG. 5, the signal processing system may calculate that the baseline is generally constant during time period 506, is changing at a particular rate during time period 516, and is generally constant during time period 510. The signal processing system may detect the rate of change in the baseline when it is changing and/or the percentage change and/or magnitude of change in the baseline between two periods where the baseline is generally constant or is changing below a threshold. In an embodiment, the signal processing system may characterize the shape of the baseline change during time period 516 using a linear (e.g. best-fit line or threshold-crossing) or non-linear characterization technique (e.g. curve fitting, template matching, adaptive methods, etc.). The characteristics of the shape of the baseline may, for example, provide information on the type of physiological event causing the baseline change. In addition, non-linear parameters associated with the baseline may also be calculated. Any other suitable processing techniques may be used in analyzing the baseline of PPG signal 500.

The signal processing system may also calculate whether there are any other signal characteristic changes before, during, and/or after a baseline change. For example, the signal processing system may calculate the amplitude of the AC component of PPG signal 500. For example, the signal processing system may calculate the average or median amplitude of the AC component over a selected amount of time or over a selected number of cardiac cycles.

The signal processing system may monitor one or more signal characteristics to detect that an event has occurred. For example, as shown in FIG. 5, both the baseline and AC component of PPG signal 500 changed between time period 506 and time period 510. The signal processing system may analyze these changes and determine that an event has occurred. For example, the signal processing system may detect that the patient has moved his position.

It will be understood that although a PPG signal is used to detect events in the discussion above, any suitable signals or devices may be used to detect events such as, for example, an electrocardiogram, electroencephalogram (EEG), electrogastrogram, electromyogram (EMG), heart rate signals, pathological sounds, ultrasound, or any other suitable biosignal, dynamic signals, non-destructive testing signals, condition monitoring signals, fluid signals, geophysical signals, astronomical signals, electrical signals, financial signals including financial indices, sound and speech signals, chemical signals, meteorological signals including climate signals, any other suitable signal, or any combination thereof.

In some embodiments, the signal processing system may detect the occurrence of an event based only on changes in the signal characteristics or changes in the baseline (e.g., changes in baseline level, rate of change of the baseline, non-linear parameters associated with the baseline, shape of the baseline change, or any combination thereof). For example, based at least in part on a portion of the signal (e.g., PPG signal 500 during time period 506), the signal processing system may calculate or use one or more predetermined thresholds. In some embodiments, if there exists a number of ordered discrete states, the signal processing system may determine that an event has occurred based on whether the signal characteristics or the baseline falls below, equals, or exceeds the threshold.

Figure 6:
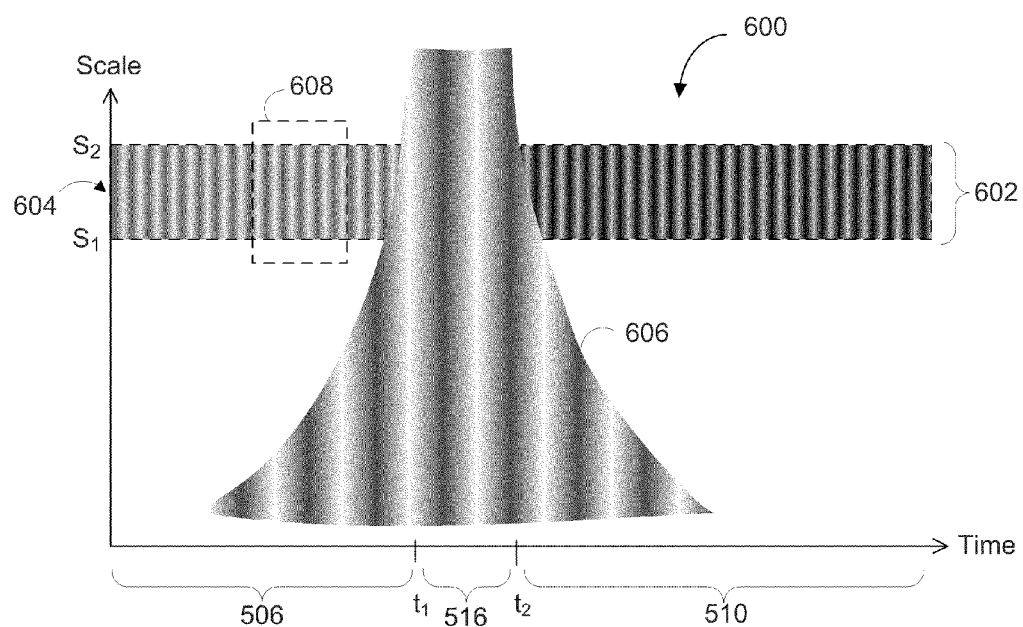
FIG. 6 shows a scalogram of a PPG signal in accordance with an embodiment.

In some embodiments, the signal processing system may also detect an event by transforming the received signal. For example, the signal processing system may transform the signal using a continuous wavelet transform. FIG. 6 shows a simplified view of a scalogram 600 generated from a continuous wavelet transform of PPG signal 500 of FIG. 5. Although the continuous wavelet transform is used in this example, any other suitable types of transforms may also be used. It will be understood that, for the sake of clarity, only the pulse band and the effect of the baseline change of PPG signal 500 is shown in FIG. 6. It will also be understood that lower energy or amplitude values in scalogram 600 are represented as lighter shades of gray and higher energy or amplitude values in scalogram 600 are represented as darker shades of gray.

For time periods 506, 510, and 516, the pulse band 602 of the PPG signal is generally located between a lower scale $S_1$ and an upper scale $S_2$ of the scalogram. As shown in FIG. 6, the lower amplitude of the AC component of PPG signal 500 during time period 506 has been transformed to lower energy or amplitude values in pulse band 602 during the same time period. Likewise, the higher amplitude of the AC component of PPG signal 500 during time period 510 has been transformed to higher energy or amplitude values in pulse band 602 during the same time period. In addition, the change in baseline of the PPG signal 500 during time period 516 has been transformed to an artifact 606 (e.g., a high energy broad-scale cone). Thus, by analyzing particular artifacts and characteristics in various regions of the scalogram, events may be detected. For example, the signal processing system may analyze the real part, imaginary part, and/or phase of the artifact in the various regions. As another example, the signal processing system may analyze characteristics such as energy parameters in the various regions.

The signal processing system may calculate any suitable energy parameter within a region on the scalogram (e.g., region 608). The size and shape of region 608 may be selected in any suitable way. For example, the height and location of region 608 may be selected to cover the pulse band 602. Pulse band 602 may vary its location and size over time. Therefore, in an embodiment, region 608 may be centered over ridge 604 of pulse band 602. The ridge of pulse band 602 may be identified, for example, using ridge following techniques or any other suitable technique such as using heart rate calculated from the PPG signal. The ridge of the pulse band may be identified, for example, using the techniques described in Watson et al., U.S. patent application Ser. No. 12/245,326, filed Oct. 3, 2008, entitled "SYSTEMS AND METHODS FOR RIDGE SELECTION IN SCALOGRAMS OF SIGNALS," which is incorporated by reference herein in its entirety. With the ridge location known, the height of region 608 may be selected to span a selected number of scales above and below the ridge. The number of scales may be selected such that region 608 spans only a portion of pulse band 602, all of pulse band 602, or all of the pulse band plus an additional amount. In an embodiment, the height and location of region 608 may be fixed to cover the range of scales where the pulse band is expected to be located. For example, the height of region 608 may span from a scale whose characteristic frequency is about 0.5 Hz to a scale whose characteristic frequency is about 4 Hz or equivalently 30-240 bpm. The width of region 608 may be selected to cover any suitable length of time, such as 1, 2, 3, 4, 5, etc. seconds. Region 608 may slide across the scalogram calculating the energy parameter in real-time or off-line. The energy parameter calculated within region 608 may be, for example, the average or median energy within the region. It will be understood that any other suitable energy parameter may also be used. The signal processing system may also calculate percent or magnitude changes in the energy parameter over time. In an embodiment, the amplitude of the ridge of the pulse band may be analyzed in place of or in addition to the energy of the pulse band.

In addition to calculating the energy parameter, the signal processing system may also detect artifacts within the scalogram, which may represent baseline changes. Artifacts may appear as a high energy broad-scale cone such as artifact 606. The system may detect the artifact in any suitable way. For example, the system may detect the artifact in response to detecting a large change in the average energy across one or more scales. As another example, the system may detect the artifact using image processing techniques. As yet another example, the system may detect the artifact in response to detecting peak values in the pulse band that are inconsistent with previous peak values. Artifacts in the scalogram may also be detected using the techniques described in Watson et al., U.S. patent application Ser. No. 12/245,336, filed Oct. 3, 2008, entitled "SYSTEMS AND METHODS FOR ARTIFACT DETECTION IN SIGNALS," which is incorporated by reference herein in its entirety. The signal processing system may calculate characteristics of an artifact such as its size, shape, and its energy parameter.

The signal processing system may monitor one or more characteristics of the scalogram to detect that an event occurred. In an embodiment, the signal processing system may monitor the energy parameter within region 608 as the region moves across scalogram 600 and the occurrence of artifacts within scalogram 600. For example, the signal processing system may determine that the energy parameter calculated for region 608 increased from time period 506 to time period 510. In addition, the signal processing system may detect an artifact during time period 516. As a result, the signal processing system may determine that an event has occurred. For example, the signal processing system may detect that the patient moved his position during time period 516.

In some embodiments, the signal processing system may detect the occurrence of an event using either the calculated energy parameters or the detected artifact. For example, based at least in part on a portion of wavelet transform 600 (e.g., a portion of region 608), the signal processing system may calculate or use one or more predetermined thresholds. If the calculated energy parameter or detected artifact exceeds a threshold, the signal processing system may determine that an event has occurred.

In some embodiments, PPG signal 500 and scalogram 600 may be used together to detect events. For example, the signal processing system may detect the event by analyzing features of both the PPG and its corresponding scalogram. As another example, the signal processing system may detect the event by utilizing portions of PPG signal 500 and wavelet transform 600. For instance, the signal portions of PPG signal 500 and wavelet transform 600. For instance, the signal processing system may determine when an artifact occurs in scalogram 600 (e.g., during time period 516). Based at least in part on this information, the signal processing system may compare signal characteristics of PPG signal 500 in the time period before the artifact (time period 506) and with signal characteristic of PPG signal 500 after the artifact (time period 510). Furthermore, the signal processing system may determine when the baseline change occurs in PPG signal 500. Based at least in part on this information, the signal processing system may calculate changes in the characteristics (e.g., energy parameters) of wavelet transform 600 in the time period before the baseline change and after the baseline change.

The detection of an event may indicate a physiological change in the user such as, for example, changes in blood pressure (systolic and diastolic changes), changes in body position (e.g., arm movement), sleep arousal, vasodilation, vasoconstriction, a sympathetic nervous response, or a parasympathetic nervous response.

Figure 7A:
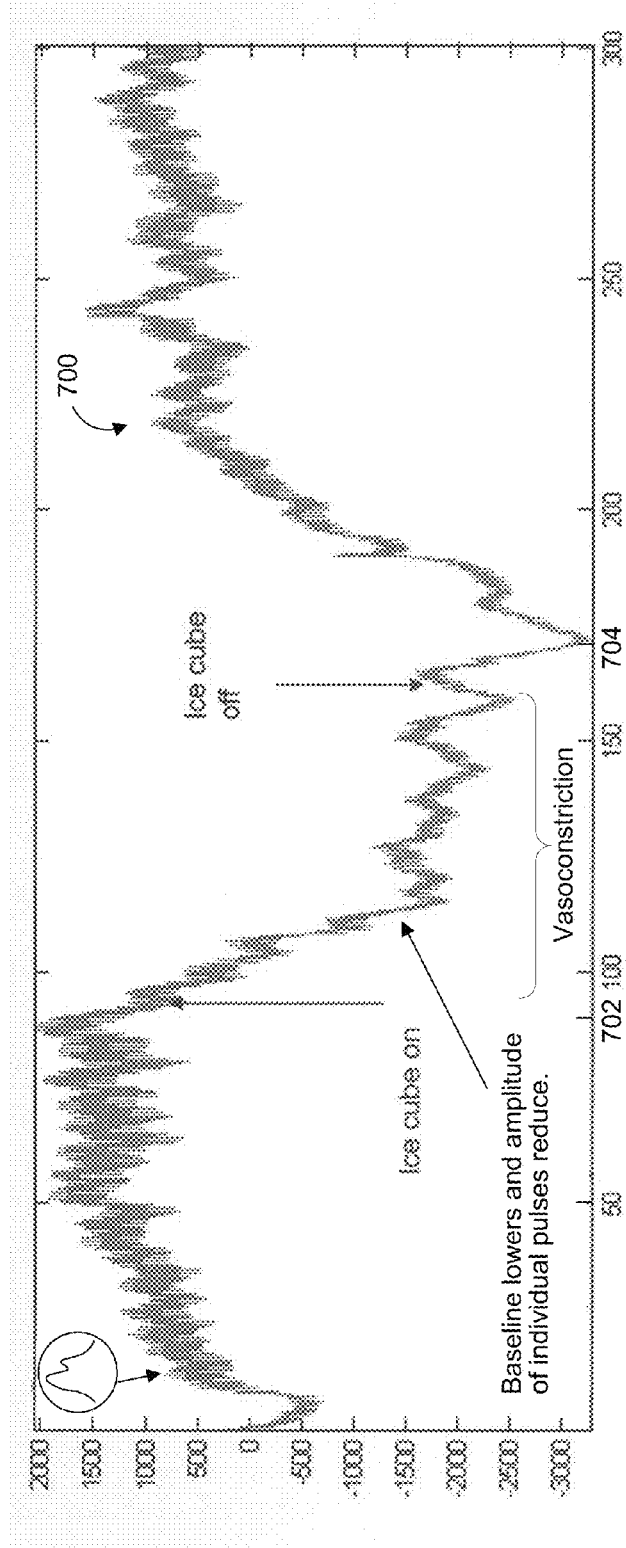
FIGS. 7A and 7B show an exemplary PPG signal and a corresponding scalogram in accordance with an embodiment.
Figure 7B:
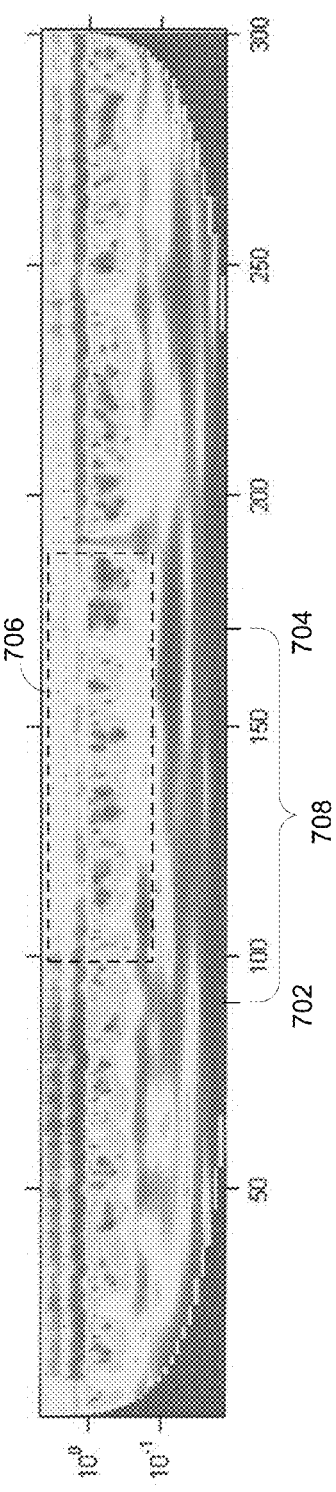

In an embodiment, detection of changes in the PPG signal and/or changes in the scalogram may be used to detect a change in blood pressure. Blood pressure changes may manifest as a pronounced and sustained change in baseline with an associated change in PPG peak to peak amplitude. For example, the administration of a vasoconstriction drug may increase blood pressure while constricting the blood vessels. The constriction of the blood vessels may manifest in a baseline change of the PPG signal (e.g., decrease in baseline), an AC component change in the pulsatile part of the PPG signal, or any combination thereof. The constriction of the blood vessels will also manifest in the detection of one or more artifacts combined with a change in the energy characteristics in the region of the scalogram associated with pulsatile activity. For example, FIG. 7A shows an exemplary PPG signal 700 obtained from a probe that has been placed on a user's index finger. When an ice cube is placed on the back of the user's hand at time 702, the baseline of PPG signal 700 and the amplitude of the AC component decreases due to vasoconstriction. Once the ice cube is removed at time 704, the baseline and the amplitude of the AC component increases to normal levels. As shown in FIG. 7B, artifacts and changes in the energy characteristics may be detected in region 706 during time period 708 (while the ice cube is on the user's hand).

Figures 8A, 8B:
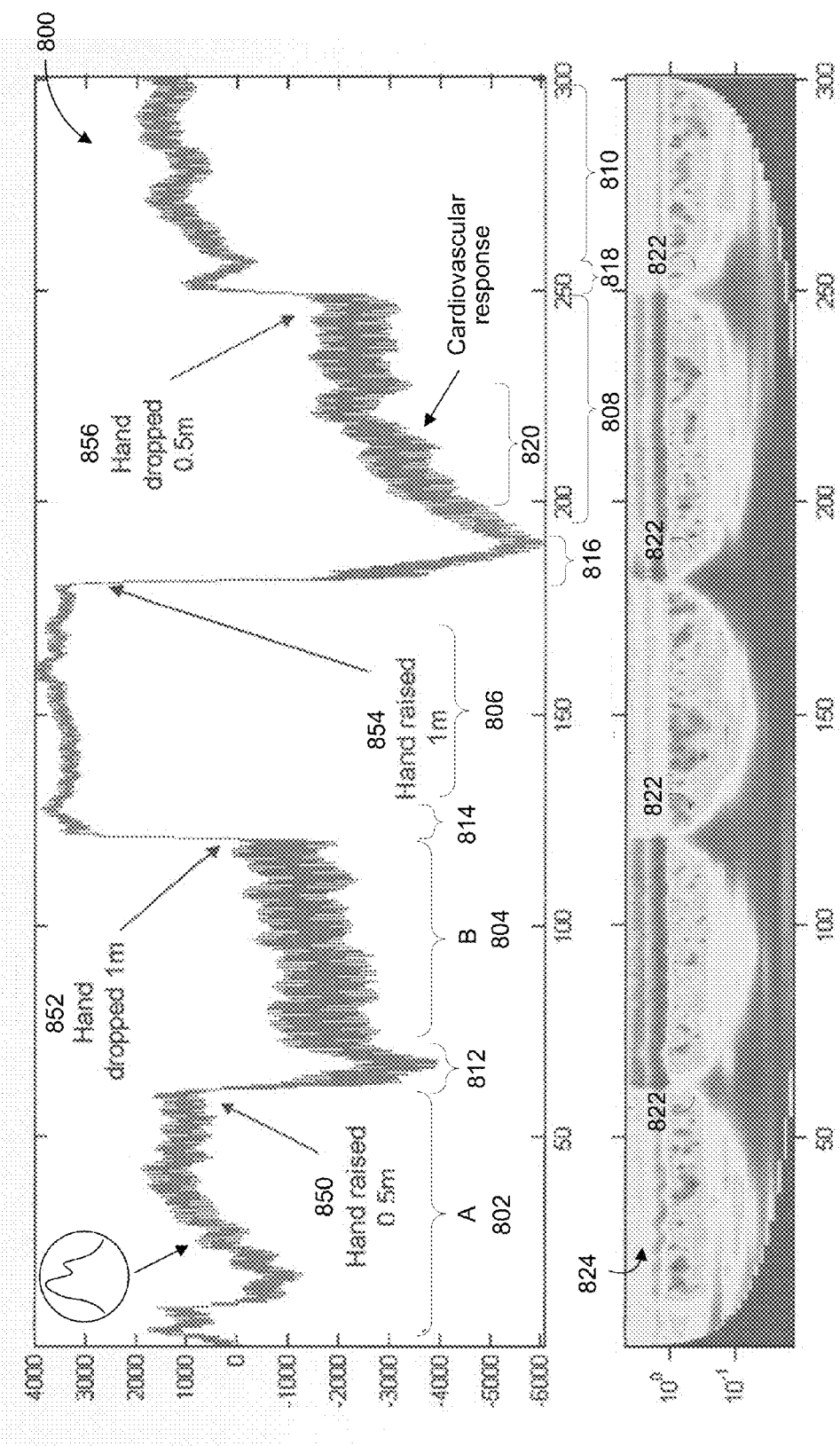
FIGS. 8A and 8B show another exemplary PPG signal and a corresponding scalogram in accordance with an embodiment.

In an embodiment, following a change in posture, the blood pressure may slowly return to (or near) its original level as a cardiovascular response to the change in posture. This may manifest in changes in calculated signal characteristics in the PPG signal, changes in baseline in the PPG signal, the detection of one or more artifacts in the scalogram, changes in characteristics in the scalogram, or any combination thereof. A change in body position may be identified through the detection of pronounced movement (e.g. high energy artifact across multiple scales of the scalogram of a the PPG) followed by baseline changes characteristic of a change in blood pressure and/or vasotone—changes associated with a change in posture. These interpretations may also be improved through the use of other monitoring devices (e.g., movement sensors (accelerometers, EMG, etc.) on the patient. For example, as shown in FIG. 8A, changes in signal characteristics in PPG signal 800 may be detected during time periods 802, 804, 806, 808, and 810. Changes in signal characteristics and changes in the baseline may be caused by changes in the height of a subjects hand. At time 850, the subject's hand was raised 0.5 meters. At time 852, the subjects band was lowered 1.0 meter. At time 854, the subject's hand was raised 1.0 meter. At time 856, the subject's hand was dropped 0.5 meter. These changes may cause baseline changes to occur that may detected during time periods 812, 814, 816, and 818. In addition, a cardiovascular response following a change in posture may be detected as PPG signal 800 settles into a new relatively steady state condition. The cardiovascular response may be seen, for example, during time period 820. As shown in FIG. 8B, artifacts 822 may be detected on scalogram 824 during each posture change. In some cases, once a change in posture has been detected, further analysis may be performed to characterize the sympathetic/parasympathetic responsiveness of the user A sympathetic response to a stimulus or stimuli may manifest as a vasoconstriction with an associated rapid increase in blood pressure which may be observed as baseline change in the PPG. A change in heart rate and/or breathing rate and/or decreasing PPG peak to peak amplitude may also be associated with the sympathetic response and may be observed in the scalogram or by another suitable means. A parasympathetic response may also be observed. This is related to a decrease in blood pressure and associated vasodilatation with a decreased baseline (blood pressure, vasodilatation, etc.) heart rate, and respiratory rate, and/or an increase in the PPG peak to peak amplitude. The measurement of the sympathetic-parasympathetic balance in response to a stimulus may prove clinically useful for the evaluation of the autonomic nervous system of a subject. Vasodilation and vasoconstriction may be typically associated with changes in blood pressure. However, changes in PPG peak to peak amplitudes without an associated change in baseline may suggest a change in vasotone without a change in blood pressure. The observance of such events in the PPG may be particularly useful following the administration of a drug, in particular a vasoactive drug, for example in monitoring its efficacy.

In an embodiment, the change in vasomotor tone and/or blood pressure during sleep can be an indicator of one or more types of events such as for example arousals, changes from one sleep stage to another, or sleep apnea events. Thus, the detection of vasomotor tone and/or blood pressure changes may manifest through changes in calculated signal characteristics in the PPG signal, changes in baseline in the PPG signal, the detection of one or more artifacts in the scalogram, changes in characteristics in the scalogram, or any combination thereof. The detection of this event may be used in a diagnostic and/or therapeutic sleep setting. For example, a polysomnograph, which may include a pulse oximeter sensor or the equivalent and other sensors, may capture a user's PPG signal while the user is participating in a sleep study. Thus, by analyzing the PPG signal and the scalogram derived from the PPG signal, the device may detect an event when the user wakes up or transitions from one sleep stage to another. Arousal during sleep, for example, may manifest as an increase in blood pressure and movement along with an increase in heart rate and respiratory rate. It is also likely that events in a PPG baseline may be correlated with other known indicators of arousal within a polysomnograph. For example, increased arousal may be correlated with increases in baseline which may indicate an increase in blood pressure which may also correlate with increased EMG and EEG activity.

In an embodiment, deep inspiratory gasps may cause marked baseline shifts. Hence, in an embodiment, the effect of irregular breaths (e.g. gasps, or single deep or shallow breaths) may be detected by changes in the baseline in either the original or transformed signal. This information is useful in the monitoring of user respiration and/or the effect of ventilation devices on the user. The inter-thoracic pressure changes caused by deep inspiratory gasps may cause associated modulations in the blood pressures of the vascular tree. These modulations may, for example, cause the modulation of the PPG baseline thereby allowing individual breaths to be monitored. Hence irregular breathing patterns may be distinguished from patterns observed in the baseline.

The foregoing detections of events may also cause an action to be performed. For example, a flag may be set that indicates that further analysis needs to be performed. As another example, the recalibration of a device may be triggered by the detection. For instance, a continuous, non-invasive blood pressure (CNIBP) monitor may be monitoring the diastolic/systolic blood pressure of a user. In response to the detection of an event (e.g., the user moving the body part attached to a probe of the CNIBP to a different location), recalibration of the CNIBP monitor may be automatically triggered.

Figure 9:
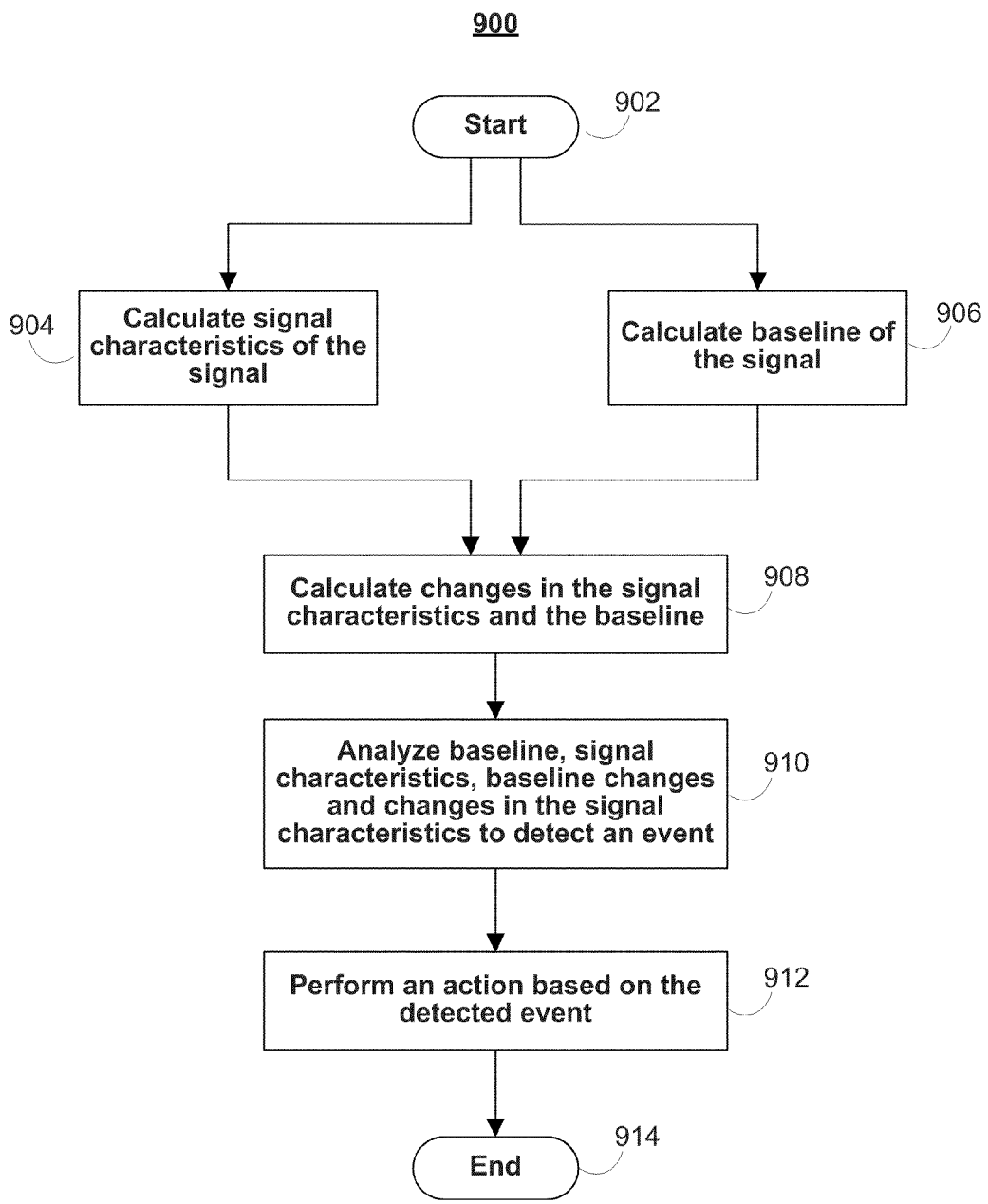
FIG. 9 shows a flowchart of an illustrative process for detecting an event in a signal in accordance with an embodiment.

FIG. 9 shows a flowchart of an illustrative process for detecting an event in a signal in accordance with an embodiment of the present disclosure. Process 900 starts at step 902. After the process starts at step 902, the process may perform steps 904 and 906 in parallel. At step 904, the signal processing system may calculate one or more signal characteristics of a signal (e.g., PPG signal 500 of FIG. 5). For example, the signal processing system may calculate the average or median value of an AC component of the signal.

At step 906, the signal processing system may calculate the baseline of the signal. The baseline may be calculated as an average or median of the signal over a selected amount of time or over any other suitable metric.

After calculating the one or more signal characteristics and the baseline of the signal, the process 900 may move to step 908. At step 908, the signal processing system may calculate changes in the one or more signal characteristics and the baseline. For example, the signal processing system may calculate the percentage or magnitude changes in the one or more signal characteristics and the baseline. After calculating the changes, process 900 may move to step 910.

At step 910, the signal processing system may analyze the calculated signal characteristics and the baseline, the baseline changes, and the changes in the signal characteristics to detect an event. For example, the system may analyze whether the changes occurred during the same time period or in a particular order. The signal processing system may use the baseline changes, the changes in the signal characteristics, the calculated signal characteristics, the calculated baseline, or any combination thereof to determine that an event has occurred. For example, the system may detect a posture change when the AC component of the signal increases after the baseline of the signal decreases. After detecting the event, process 900 moves to step 912.

In an embodiment, at step 912, the signal processing system may perform an action based at least in part on the detected event. For example, the signal processing system may recalibrate a device (e.g., a CNIBP monitor) based on the detected event. As another example, the signal processing system may set a flag at the detected event so that further analysis of the signal can be performed. For instance, if the detected event is sleep arousal, the signal processing system may perform an analysis of the sleep patterns of the user. After the action has been performed, process 900 ends at step 914.

Figure 10:
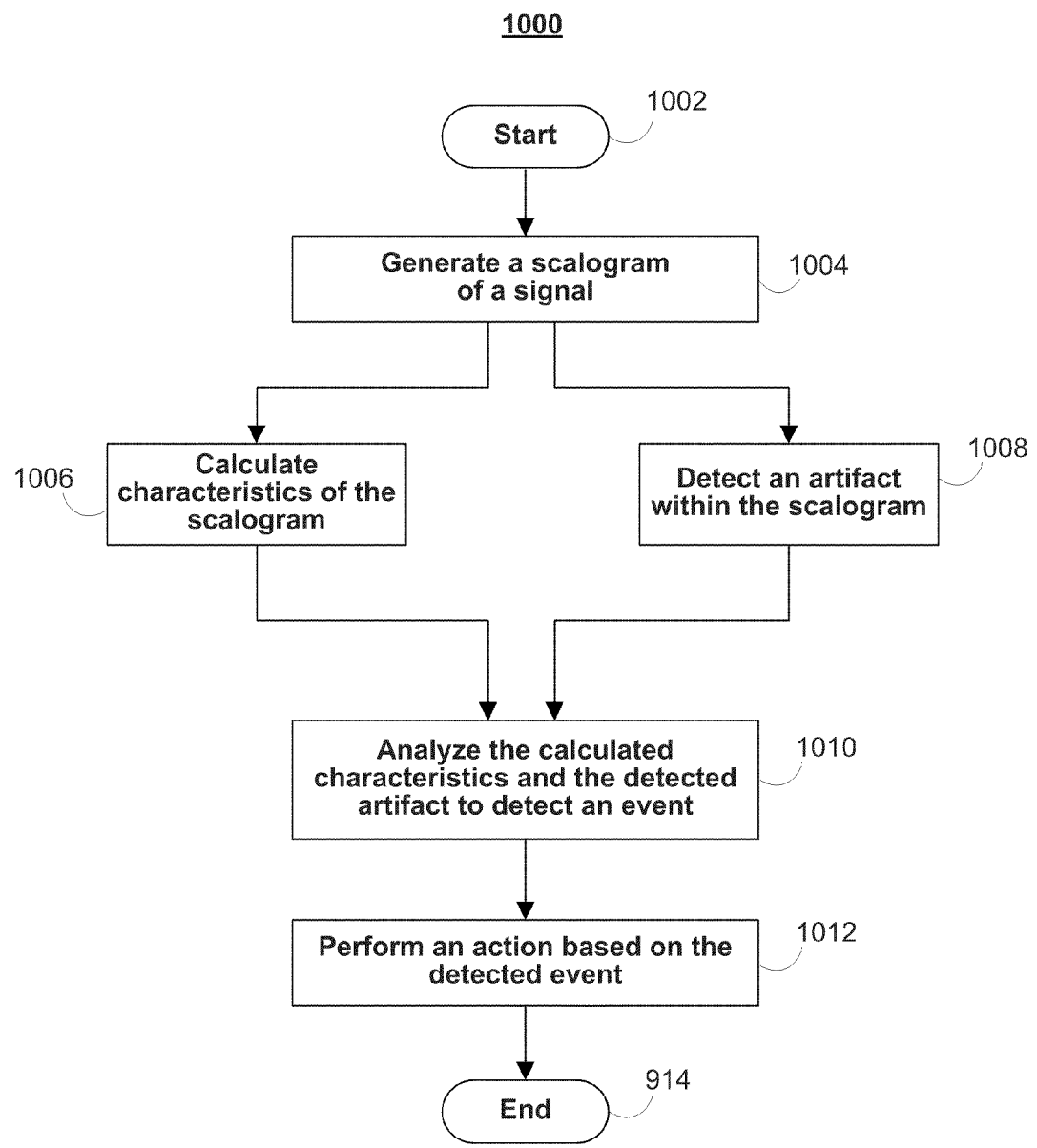
FIG. 10 shows a flowchart of an illustrative process for detecting an event in a scalogram in accordance with an embodiment.

FIG. 10 shows a flowchart of an illustrative process for detecting an event in a scalogram in accordance with an embodiment of the present disclosure. Process 1000 starts at step 1002.

At step 1004, a scalogram may be generated from a signal. The signal may be any suitable signal such as for example a PPG signal (e.g., PPG signal 500 of FIG. 5). The scalogram may be generated by performing a wavelet transformation of the PPG signal. The wavelet transform may, for example, be a continuous or discrete wavelet transform. After the scalogram has been generated, the process may perform steps 1006 and 1008 in parallel.

At step 1006, the signal processing system may calculate characteristics of the scalogram such as an energy parameter within a region (e.g., region 608 of FIG. 6) of the scalogram. The size and shape of the region may be selected in any suitable way. For example, the height and location of the region may be fixed or may be dynamically changed to cover a band or region of interest in the scalogram.

At step 1008, the signal processing system may detect an artifact within the scalogram. For example, the signal processing system may detect a high energy broad-scale cone (e.g., artifact 606 of FIG. 6) on the scalogram.

After calculating the characteristics and detecting the artifact within the scalogram, the process may move to step 1010. At step 1010, the signal processing system may analyze the calculated characteristics and the detected artifact to detect an event. In an embodiment, the system may use calculated energy parameters, the detected artifact, or any combination thereof to determine that an event has occurred. After detecting the event, process 1000 moves to step 1012.

At step 1012, the signal processing system may perform an action based at least in part on the detected event. The actions that may be performed may be similar to actions described in step 912 of process 900 (FIG. 9). For example, the signal processing system may recalibrate a device based on the detected event. As another example, the signal processing system may set a flag at the detected event so that further analysis of the signal can be performed. After the action has been performed, process 1000 then ends at step 1014.

The signal processing system may also detect the event by analyzing an original signal and the transform of that signal. For example, the signal processing system may determine when an artifact in the transform occurs. Based at least in part on this information, the signal processing system may analyze changes in the signal characteristics of the original signal before and after the occurrence of the artifact to determine whether an event occurs. For example, the signal characteristics (e.g., the AC component) of the original signal prior to the occurrence of the artifact may be compared to the signal characteristics (e.g., the AC component) of the original signal after the occurrence of the artifact. In addition, the signal processing system may determine when the baseline change occurs in the original signal. Based at least in part on this information, the signal processing system may analyze changes in a characteristic of the wavelet transform (e.g., energy within a particular region) before and after the baseline change to determine whether an event occurs.

It will be understood that the foregoing is only illustrative of the principles of the disclosure, and that the disclosure can be practiced by other than the described embodiments, which are presented for purposes of illustration and not of limitation.

What is claimed is:
1. A method of detecting the occurrence of events from a signal, comprising:
receiving the signal;
transforming, using a processor, the signal to generate a transformed signal;
generating, using the processor, a scalogram based at least in part on the transformed signal;
detecting an artifact within the scalogram, wherein the artifact is a high-energy broad-scale cone shaped region of the scalogram;
calculating characteristics of the detected artifact; and
analyzing, using the processor, the characteristics of the detected artifact within the scalogram to detect an occurrence of a physiological event.

2. The method of claim 1, further comprising:
calculating a first energy parameter within a first region of the scalogram;
calculating a second energy parameter within a second region of the scalogram subsequent to the artifact; and
further analyzing the first and second energy parameters to detect the occurrence of the event.

3. The method of claim 2, wherein the first energy parameter is the average energy within the first region and the second energy parameter is the average energy within the second region.

4. The method of claim 2, wherein the signal is a photoplethysmograph and wherein the first and second regions comprise at least a portion of a pulse band.

5. The method of claim 4, wherein the first and second regions comprise a ridge of the pulse band.

6. The method of claim 1, wherein the event comprises at least one of changes in blood pressure, changes in body position, vasodilation, vasoconstriction, sympathetic nervous response, parasympathetic nervous response, and sleep arousal.

7. The method of claim 1, further comprising performing an action based at least in part on the detected event.

8. The method of claim 7, wherein performing the action comprises recalibrating a device based at least in part on the detected event or setting a flag of the detected event.

9. The method of claim 1, further comprising:
calculating at least one signal characteristic of the signal; and
further analyzing the at least one signal characteristic to detect the occurrence of the event.

10. The method of claim 1, further comprising:
detecting a baseline change in the signal;
calculating a first energy parameter within a first region of the scalogram;
calculating a second energy parameter within a subsequent second region of the scalogram subsequent; and
further analyzing the baseline change and the first and second energy parameters to detect the occurrence of the event.

11. A system for detecting the occurrence of events from a signal, comprising:
a signal generator capable of generating the signal; and
a processor capable of:
transforming the signal to generate a transformed signal;
generating a scalogram based at least in part on the transformed signal;
detecting an artifact within the scalogram, wherein the artifact is a high-energy broad-scale cone shaped region of the scalogram;
calculating characteristics of the detected artifact; and
analyzing, using the processor, the characteristics of the detected artifact within the scalogram to detect an occurrence of a physiological event.

12. The system of claim 11, wherein the processor is further capable of:
calculating a first energy parameter within a first region of the scalogram;
calculating a second energy parameter within a second region of the scalogram subsequent to the artifact; and
further analyzing the first and second energy parameters to detect the occurrence of the event.

13. The system of claim 12, wherein the first energy parameter is the average energy within the first region and the second energy parameter is the average energy within the second region.

14. The system of claim 12, wherein the signal is a photoplethysmograph and wherein the first and second regions comprise at least a portion of a pulse band.

15. The system of claim 14, wherein the first and second regions comprise a ridge of the pulse band.

16. The system of claim 12, wherein the artifact is a high energy broad-scale cone.

17. The system of claim 11, wherein the event comprises at least one of changes in blood pressure, changes in body position, vasodilation, vasoconstriction, sympathetic nervous response, parasympathetic nervous response, and sleep arousal.

18. The system of claim 11, wherein the processor is further configured to initiate an action based at least in part on the detected event.

19. The system of claim 18, wherein the action comprises recalibrating a device based at least in part on the detected event or setting a flag of the detected event.

20. The system of claim 11, wherein the processor is further capable of:
calculating at least one signal characteristic of the signal; and
further analyzing the at least one signal characteristic to detect the occurrence of the event.

21. The system of claim 11, wherein the processor is further capable of:
detecting a baseline change in the signal;
calculating a first energy parameter within a first region of the scalogram;
calculating a second energy parameter within a subsequent second region of the scalogram subsequent; and
further analyzing the baseline change and the first and second energy parameters to detect the occurrence of the event.

22. A non-transitory computer-readable medium for use in detecting the occurrence of events from a signal, the computer-readable medium having computer program instructions recorded thereon for:
receiving the signal;
transforming the signal to generate a transformed signal;
generating a scalogram based at least in part on the transformed signal;
detecting an artifact within the scalogram, wherein the artifact is a high-energy broad-scale cone shaped region of the scalogram;
calculating characteristics of the detected artifact; and
analyzing, using the processor, the characteristics of the detected artifact within the scalogram to detect an occurrence of a physiological event.

* * * * *